United States Patent
Barnicki et al.

(10) Patent No.: US 6,500,970 B1
(45) Date of Patent: Dec. 31, 2002

(54) RECOVERY AND PURIFICATION OF 3,4-EPOXY-1-BUTENE USING HIGH-BOILING SOLVENTS

(75) Inventors: Scott Donald Barnicki, Kingsport, TN (US); Jerome Leonard Stavinoha, Jr., Longview, TX (US); Robert Sterling Kline, Talbott, TN (US); Jackie Lee Hamilton, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/910,330

(22) Filed: Jul. 20, 2001

(51) Int. Cl.[7] .............................................. C07D 301/32
(52) U.S. Cl. ........................ 549/538; 549/534; 549/536; 549/541
(58) Field of Search ................................ 549/538, 534, 549/536, 541

(56) References Cited

U.S. PATENT DOCUMENTS

| | | |
|---|---|---|
| 2,773,844 A | 12/1956 | Carlson et al. |
| 3,418,338 A | 12/1968 | Gilman et al. |
| 3,644,432 A | 2/1972 | Hoch et al. |
| 3,745,092 A | 7/1973 | Vanderwater |
| 3,948,621 A | 4/1976 | Cocuzza et al. |
| 3,962,136 A | 6/1976 | Nielsen et al. |
| 3,964,980 A | 6/1976 | Ozero |
| 4,221,727 A | 9/1980 | Tsang et al. |
| 4,233,221 A | 11/1980 | Raines et al. |
| 4,356,312 A | 10/1982 | Nielsen et al. |
| 4,437,938 A | 3/1984 | Bhise et al. |
| 4,437,939 A | 3/1984 | Bhise et al. |
| 4,897,498 A | 1/1990 | Monnier et al. |
| 4,950,773 A | 8/1990 | Monnier et al. |
| 5,081,096 A | 1/1992 | Monnier et al. |
| 5,117,012 A | 5/1992 | Stavinoha, Jr. et al. |
| 5,312,931 A | 5/1994 | Stavinoha, Jr. |
| 5,529,667 A | 6/1996 | Coffey |
| 5,559,255 A | 9/1996 | Kawabe et al. |
| 5,618,954 A | 4/1997 | Boeck et al. |
| 6,018,061 A | 1/2000 | Barnicki et al. |

OTHER PUBLICATIONS

Dever et al., Ethylene Oxide, Kirk–Othmer Encyclopedia of Chemical Technology, 4th Ed., vol. 9, 1994, pp. 925–939.
Kister, H.Z. Distillation Design, McGraw–Hill, N.Y. (1992), Chapter 6.
Kister, H.Z. Distillation Design, McGraw–Hill, N.Y. (1992), Chapter 8.

*Primary Examiner*—Ba K. Trinh
(74) *Attorney, Agent, or Firm*—Michael J. Blake; Bernard J. Graves, Jr.

(57) ABSTRACT

Disclosed is a process of recovering 3,4-epoxy-1-butene (epoxybutene) from an epoxybutene-laden reaction product gas by absorption into a high-boiling solvent. Also disclosed is a process for the purification of the epoxybutene by separating epoxybutene from the solvent and other reaction by-products by a novel combination of distillation and decantation steps.

18 Claims, 1 Drawing Sheet

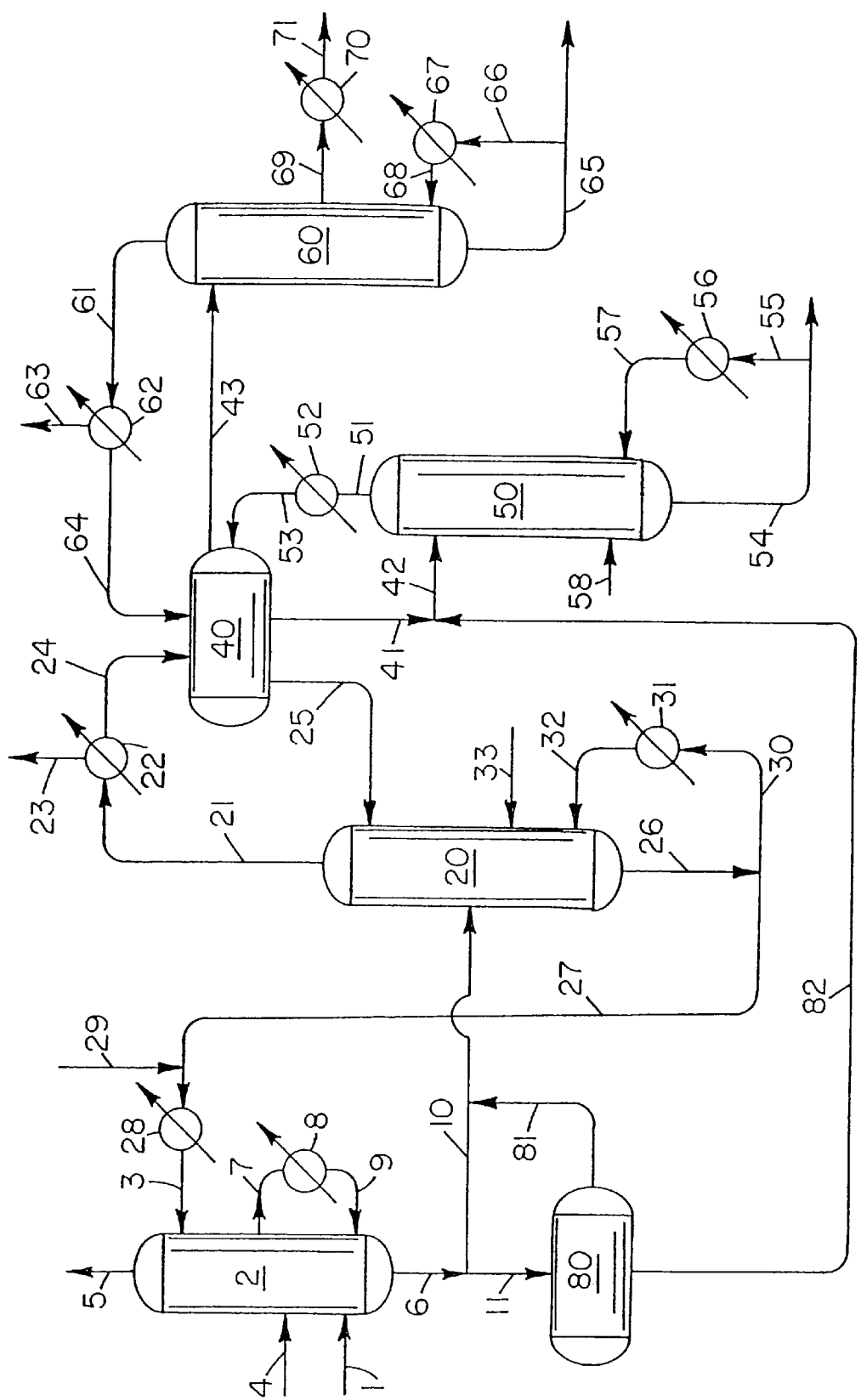

RECOVERY AND PURIFICATION OF 3,4-EPOXY-1-BUTENE USING HIGH-BOILING SOLVENTS

FIELD OF THE INVENTION

The present invention pertains to a process of recovering and purifying 3,4-epoxy-1-butene (epoxybutene) from a reaction product gas, obtained by the vapor phase catalytic partial oxidation of 1,3-butadiene with oxygen over a silver catalyst. More specifically, the present invention pertains to a process of recovering epoxybutene from an epoxybutene-laden reaction product gas by absorption into a high-boiling solvent. This invention also pertains to a method of separating epoxybutene from the solvent and other reaction by-products by a novel combination of distillation and decantation steps.

BACKGROUND OF THE INVENTION

Ethylene oxide (EO) and epoxybutene both may be produced in large scale plants by similar catalytic partial oxidations of the corresponding olefin with oxygen over a silver catalyst. See for example, U.S. Pat. Nos. 2,773,844 and 3,962,136, and 4,356,312 for EO and U.S. Pat. Nos. 4,897,498, 4,950,773, and 5,081,096 for epoxybutene. Considerable effort has been devoted to the development of efficient methods of recovering these epoxides, particularly EO, from the reaction product gas and subsequent purification of the epoxide.

According to U.S. Pat. Nos. 3,745,092 and 3,964,980 and Dever et al. *Ethylene Oxide*, in *Kirk-Othmer Encyclopedia of Chemical Technology*, 4th Ed., 1994, pp. 929–930, EO is recovered and purified according to the following procedure. A reaction product gas containing typically 0.5 to 5% EO, obtained by the vapor phase catalytic oxidation of ethylene with oxygen over a silver catalyst, is introduced to an EO absorption tower where it is contacted counter-currently with an absorbent comprised mostly of water, within which the EO is absorbed. The absorber is typically maintained at a temperature of 5 to 40° C. and 10 to 30 bars absolute (bara).

The EO-laden absorbent is then sent to a stripping column where vaporous EO is recovered from the top of the tower at a temperature of 85 to 140° C. by steam stripping at reduced pressure. The water remaining after the distillation of EO is recycled to the absorption tower for reuse. EO reacts readily with water under absorption and distillation conditions to form ethylene glycol, which can react further to form diethylene glycol, triethylene glycol, and higher oligomers. Although ethylene glycol is a valuable and marketable chemical, diethylene glycol and higher oligomers have much less commercial demand and are thus generally undesirable by-products. Formation of ethylene glycol oligomers can be controlled to some extent by limiting ethylene glycol concentration in the recycled water to the absorber. Typical levels are less than 10 weight per cent ethylene glycol in the recycled absorber water.

The crude EO vapor recovered in the stripper overhead comprises EO as the main component, as well as impurities such as water, argon, nitrogen, carbon dioxide, methane, ethane and ethylene, formaldehyde, and acetaldehyde. The light or low-boiling components, e.g., nitrogen, carbon dioxide, argon, methane, ethane, and ethylene are removed overhead in a second stripping column. The partially purified EO is removed from the lower section of base of the second stripping column and is transferred to the mid-section of a refining column for final purification. U.S. Pat. Nos. 5,529,667 and 3,418,338 disclose the use of extractive distillation with water as a solvent in either the second stripping column or the refining column to reduce the level of aldehyde impurities in the final purified EO product.

By employing the above-described procedure, EO purities of greater than 99.5 mole per cent are possible. Although these water-based processing steps function effectively for EO recovery and purification, they cannot be employed equally efficaciously for the recovery and purification of epoxybutene. Firstly, whereas EO is completely and infinitely miscible with water, epoxybutene is only sparingly miscible with water. At 25° C., the solubility of epoxybutene in water is only about 5 to 6 weight percent. As a result, water is a very poor absorbent for epoxybutene. High water to epoxybutene ratios, e.g., upward of 50/1 to 150/1, are required to ensure complete absorption of epoxybutene from the reaction off gas. Such ratios are prohibitive from equipment cost and energy usage standpoints.

Secondly, EO is a relatively low-boiling component compared to water, i.e., normal boiling point of 10.4° C. versus 100° C., respectively, and does not form an azeotrope with water. Thus, EO can be distilled readily from water by simple fractional distillation techniques as described above for the conventional EO recovery scheme. However, epoxybutene is much more hydrophobic than EO and forms a minimum-boiling azeotrope with water. High purity epoxybutene cannot be obtained by the simple fractional distillation techniques employed for EO recovery.

Other methods proposed for recovery of EO from ethylene oxidation effluents likewise are not effective or are uneconomical for epoxybutene recovery and purification. For example, U.S. Pat. No. 3,948,621 discloses a method of separating EO and carbon dioxide simultaneously from a mixed gas obtained from catalytic oxidation of ethylene by oxygen using methanol as an absorbent. As with water, epoxybutene forms a minimum-boiling azeotrope with methanol and, thus, epoxybutene and methanol cannot be separated readily by simple fractional distillation.

U.S. Pat. Nos. 4,437,938 and 4,437,939 disclose methods using supercritical or near supercritical carbon dioxide and water at the same time as absorbents. EO is first absorbed into water as in conventional recovery methods. The EO-rich aqueous absorbent contacted with (near) supercritical carbon dioxide, and EO is extracted to the carbon dioxide solvent. The carbon dioxide is separated from EO by distillation under reduced pressure. The carbon dioxide is recompressed before recycling as the extraction solvent. This method, however, has many drawbacks. First, the required amount of (near) supercritical carbon dioxide is approximately 35 times the amount of EO to be absorbed therein, resulting in large equipment. The extraction is carried out at high pressures, e.g., 86 bara, while the distillation step is carried out at lower pressure, i.e., about 0.1 to 2 bara. The wide pressure swings results in high compression costs and thus does not provide an economical solution.

U.S. Pat. Nos. 4,221,727 and 4,233,221 discloses an EO recovery method that uses ethylene carbonate as an absorbent for EO. Ethylene carbonate has many advantages as an absorbent. The absorption affinity of ethylene carbonate for EO is higher than that of water. The vapor pressure of ethylene carbonate is quite low, i.e., normal boiling point of 239° C., so losses into the recycle gas are minimal. Moreover, ethylene carbonate is stable and does not directly react with EO. The process disclosed in U.S. Pat. No.

4,233,221, however, has the following drawbacks for EO and epoxybutene recovery. The most preferred temperature range for operation of conventional water absorption of EO is 5 to 40° C. The melting point of ethylene carbonate is 39° C., so ethylene carbonate would be a solid over almost all of the preferred temperature range. In order to avoid solidification it is necessary to operate the absorber and other processing equipment substantially above, i.e., at least 10 to 20° C., above the melting point of ethylene carbonate. This is much higher temperature than an operation using water. The absorbing power of the ethylene carbonate correspondingly decreases so that the amount of circulating absorbent must be increased, reducing the economic utility of the process.

U.S. Pat. No. 5,559,255 describes the use of propylene carbonate as an absorbent for EO. The EO-laden propylene carbonate is stripped with an inert gas to recover EO and the water by-product from the epoxidation reactor as a vapor. Purified EO is produced from the mixed water-EO vapors as in conventional methods described in U.S. Pat. Nos. 3,745,092 and 3,964,980. Unlike ethylene carbonate, propylene carbonate is a liquid at room temperature and thus offers a more robust process than ethylene carbonate absorption. However, the process described In U.S. Pat. No. 5,559,255 also has drawbacks for epoxybutene recovery and purification. Epoxybutene is a much less volatile component than EO and cannot be removed effectively from propylene carbonate by inert gas stripping as described in the '255 patent. Moreover, this EO process does not presage or address the problems associated with epoxybutene recovery and separation from the epoxybutene-water azeotrope, butadiene, or other impurities absorbed with epoxybutene from the epoxidation reactor product gas.

U.S. Pat. No. 3,644,432 discloses the use of liquid ethane as an absorbent for EO. The reactor product gas is cooled, compressed, and then passed through a molecular sieve drier bed to remove the by-product water of reaction. The dried reactor product gas is contacted in a countercurrent absorption tower with liquid ethane at a preferred temperature range of –31.5 to –17.6° C. at a pressure of about 1.8 MPa. EO is much more soluble in liquid ethane than in water, so the solvent to feed gas ratio of the absorber can be reduced considerably from the water absorbent case, with concomitant cost reductions. However, maintenance of such cryogenic temperatures expensive refrigeration equipment and much more than offsets any savings due to lower solvent to feed gas ratios. Thus, there are no acceptable EO absorption/separation methods that can be adapted readily and economically to epoxybutene absorption/separation.

The patent literature is not as extensive for epoxybutene production, but several patents describe the recovery and separation of epoxybutene. U.S. Pat. Nos. 5,117,012 and 5,312,931 disclose the use of liquid butadiene and butadiene/butane mixtures as an absorbent for epoxybutene. The reactor product gas is cooled, compressed, and contacted in a countercurrent absorption tower with liquid butadiene/n-butane at a preferred temperature range of 0.0 to 30° C. at a pressure of about 5 to 15 bara. Water and water-soluble impurties are removed by decantation of the epoxybutene-rich absorbent stream. Any remaining water, butadiene/n-butane absorbent, and low-boiling impurities are removed by distillation to give a purified EpB product. However, n-butane and 1,3-butadiene have relatively high volatilities, with normal boiling points of –0.5° C. and 4.5° C., respectively. In order to ensure that the solvent n-butane/butadiene largely remains a liquid within the absorption zone at operating temperatures that can be achieved with an inexpensive cooling medium such as water, i.e., above at least about 30° C., the absorption zone must be operated at a pressure of at least about 4.2 bara. Operation at lower pressures, and concomitantly lower temperatures is quite costly if the required low temperature cooling is supplied by ordinary means to those skilled in the art such as chilled brine or glycol refrigeration units. Thus, to meet the aforementioned temperature and pressure requirements for absorption with n-butane, the reactor effluent must first be compressed to a suitable pressure, i.e., greater than about 4.2 bara, prior to its introduction into the absorption zone. The higher pressures and resulting polytropic temperature rise within the compression zone in the presence of high concentrations of epoxybutene can cause formation of polymeric materials that deposit on the walls of the compressor and associated piping. The build-up of such polymeric material reduces the operating efficiency of the compressor and can lead to permanent equipment damage and frequent process shutdowns for maintenance, with subsequent loss of production and revenues. Moreover, the large inventory in the absorption/distillation of highly volatile and explosive butadiene and butane is dangerous and leads to higher than average safety-related costs.

U.S. Pat. No. 6,018,061 addresses the problems inherent with the compression of high concentrations of EpB, as exemplified in U.S. Pat. Nos. 5,117,012 and 5,312,931, by providing a compression or absorption refrigeration cycle for cooling the epoxybutene absorption zone prior to compression with the reaction diluent, e.g., a C3 to C5 hydrocarbon, preferably butane/butadiene, as the refrigerant. In this fashion, the epoxybutene absorption zone can be operated at pressures less than about 4 bara and a temperature of less than about 40° C. without the need for pre-compression or external refrigeration. However, this process also has disadvantages. With pressures in the absorption zone higher than the 4 bara specified in the '061 patent, the auto-cooling effect provided by the refrigeration cycle is greatly diminished. The temperature of the absorber becomes hotter and the absorptive power of the solvent, i.e., butane/butaidiene is greatly reduced. Thus, for example, at a pressure of 5.5 bara (80 pounds per square inch—psia), the auto-refrigeration effect provides only a temperature of about 60° C. Moreover, at pressures above 4 bara, the potential for unwanted condensation of n-butane/butadiene in equipment in the recycle loop increases dramatically. Excessive condensation can cause the recycle gas composition to become flammable, an unsafe and unacceptable operating condition. Finally, as with the '012 and '931 patents the inventory of highly volatile and explosive butadiene and butane is large.

U.S. Pat. No. 5,618,954 discloses the recovery of epoxybutene from a butacliene epoxidation reactor effluent gas by countercurrent contact in an absorption zone using a solvent comprising water as a primary component. Epoxybutene is recovered from the water by stripping with an inert gas, similar to the conventional EO recovery process described above. As explained above, water by itself is a poor absorbent for epoxybutene and its use results in uneconomical process due to the required high water to epoxybutene ratio. Moreover, the process as described in the '954 patent is incomplete and cannot provide purified epoxybutene. No mention is made of the binary epoxybutene-water minimum-boiling azeotrope nor of methods tc obtain purified epoxybutene from this azeotrope with water.

In view of the recovery processes described above, it is apparent that there is a need for an improved process for the efficient and economical recovery and purification of epoxybutene from the product gas of a vapor phase epoxidation reactor.

BRIEF SUMMARY OF THE INVENTION

It has been discovered that epoxybutene can be recovered from a substantially vaporous epoxidation effluent comprising epoxybutene, oxygen, butadiene, and inert reaction diluent, e.g., methane, ethane, nitrogen, and the like, by intimately contacting the vaporous effluent with an effective amount of a high-boiling liquid absorbent or solvent in an absorption zone, such as an absorber, to absorb essentially all of the epoxybutene present in the vaporous reactor effluent. The present invention therefore provides a process for the recovery of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises feeding the effluent to an absorption vessel wherein the effluent is intimately contacted with a high-boiling, liquid absorbent to obtain:

(1) a gaseous effluent comprising butadiene, oxygen and an inert diluent from the upper section of the absorption vessel; and
(2) a liquid effluent comprising epoxybutene, the absorbent and water from the lower section of the absorption vessel;

wherein the absorbent has a boiling point at ambient pressure of at least 100° C.; epoxybutene is 3,4-epoxy-1-butene; and butadiene is 1,3-butadiene.

A second embodiment of the present invention provides for the recovery and purification of epoxybutene from the above-described substantially-gaseous effluent from an epoxidation zone by the steps of:

I. feeding the effluent to an absorption vessel wherein the effluent is intimately contacted with a high-boiling, liquid absorbent to obtain (1) a gaseous effluent comprising butadiene, oxygen and an inert diluent from the upper section of the absorption vessel and (2) a liquid effluent comprising epoxybutene, the absorbent and water from the lower section of the absorption vessel;
II. feeding the liquid effluent (2) of step I, to the middle section of a first distillation column to obtain (1) a distillate effluent comprising epoxybutene and water from the upper section of the distillation vessel and (2) a liquid effluent comprising the absorbent from the lower section of the distillation vessel;
III. allowing distillate (1) from step II to form 2 phases comprising an epoxybutene-rich phase and a water-rich phase; and
IV. feeding the epoxybutene-rich phase from step III to the upper section of an epoxybutene purification distillation column to obtain (1) a distillate effluent comprising epoxybutene and water from the upper section of the distillation vessel; and (2) an effluent comprising (a) liquid epoxybutene from the lower section of the distillation column or (b) liquid or gaseous epoxybutene from the side of the distillation column;

wherein the absorbent has a boiling point at ambient pressure of at least 100° C.; epoxybutene is 3,4-epoxy-1-butene; and butadiene is 1,3-butadiene. Additional embodiments of the invention include the refining of the water-rich phase obtained from step II and the removal of absorbent present in effluent comprising butadiene, oxygen and an inert diluent from the upper section of the absorption vessel.

BRIEF DESCRIPTION OF THE DRAWING

The accompanying FIGURE is a process flow diagram illustrating an epoxybutene recovery system embodying the principles of the processes of the present invention. While the present invention is susceptible to embodiment in various forms, there is shown in the FIGURE and hereinafter described in detail preferred embodiments of the invention. However, the present disclosure is to be considered as an exemplification of the invention without limitation to the specific embodiments illustrated.

DETAILED DESCRIPTION

The process of the present invention may be used in combination with any epoxidation process wherein butadiene is contacted with an oxygen-containing gas in the presence of a catalyst and an inert gas to produce a gaseous, epoxidation effluent comprising epoxybutene, oxygen, unreacted butadiene, and reaction diluent, e.g., nitrogen, carbon dioxide, methane, ethane, propane, n-butane, or other species inert under reaction conditions. The silver-catalyzed, epoxidation processes described in U.S. Pat. Nos. 4,897,498 and 4,950,773 are typical of those that may be employed in the epoxidation zone. The epoxidation zone comprises one or more reactors of any design that allows removal of the heat of reaction in order to prevent an exothermic temperature excursion from occurring. For example, a shell-and-tube design, typically used for ethylene oxide production, may be employed. Other types of reactor designs include multi-staged adiabatic reactors, fluidized bed reactors, moving or transport bed reactors and the like.

The feed to the epoxidation zone comprises butadiene, an oxygen-containing gas and an inert diluent gas in various proportions. Generally, any oxygen ($O_2$) concentration up to the explosive limit can be used. For example, when using nitrogen as the inert gas, the maximum oxygen concentration normally is in the range of about 9 mole percent. Higher oxygen concentration, e.g., up to about 18 mole percent, may be employed using methane as the inert diluent. When using butane as the inert diluent gas, relatively high oxygen concentrations, e.g., up to about 30 mole percent may be employed. The recovery process of the present invention advantageously is used in combination with a butadiene epoxidation process employing carbon dioxide, nitrogen, ethane, or preferably, methane as the inert diluent. The butadiene concentration typically is about 4 to 50 mole percent. The butadiene:oxygen mole ratio in the feed normally is maintained within the range of about 1:5 to 10:1. The inert gas usually constitutes about 25 to 85 mole percent of the total feed to the epoxidation zone. Normally, the feed also includes a small amount, e.g., 1 to 40 parts per million (ppm), of a halide source such as 1,2-dichloroethane. Various other organic halides may be used, many of which are described in U.S. Pat. No. 4,950,773. The concentration of the organic halide in the feed more commonly is in the range of 2 to 10 ppm. The feed also may contain minor amounts, e.g., 5 mole percent or greater, of impurities such as up to about 4 mole percent water and up to 2 mole percent carbon dioxide. Some argon may also be present in the feed. The amount of argon is controlled by purging a small amount of the recycle gas. Typically, the amount of argon is maintained at less than 10 percent.

The gaseous epoxidation effluent typically contains from about 0.5 to about 10 mole percent EpB and preferably from about 1 to 7 mole percent, about 4 to 50 mole percent butadiene, and about 25 to 85 mole percent reaction diluent gas, e.g., nitrogen, carbon dioxide, methane, ethane, propane, n-butane, or other species inert under reaction conditions. As noted above, the diluent gas, for the purpose of the present invention, preferably is carbon dioxide, nitrogen, ethane, or most preferably, methane. The effluent also contains a total of about 0.5 to 10 mole percent of other constituents such as, water, acrolein, furan, vinylacetaldehyde, and crotonaldehyde, formed in the epoxidation reactor. Unconsumed organic halide also is present in the epoxidation effluent. The hot epoxidation effluent, typically 170 to 270° C., more typically 200 to 250° C., may be cooled in a heat exchanger by indirect contact with a suitable cooling media such as water, chilled brine, glycol, or cool reactor feed gas, to a temperature of less than 150° C., preferably less than 100° C.

The absorption zone comprises a columnar, pressure vessel containing trays or a packing material that facilitates intimate gas/liquid contact. Depending on the choice of absorbent and the absorbent flow rate, the absorber typically contains trays or packing equivalent to 5 to 25 theoretical equilibrium stages, more preferably 7 to 20 theoretical stages. The absorption vessel normally is provided with means, such as a disengaging space above the packing, to prevent or minimize entrainment of liquids in the gas stream removed from the upper section thereof. The pressurized, cooled, substantially gaseous, epoxidation effluent is fed to the lower section of the absorption vessel, preferably near the bottom of the vessel. A high-boiling, liquid absorbent is fed to the upper section, preferably near the top, of the absorption vessel and flows downward, thereby absorbing or scrubbing the epoxybutene component from the upwardly-flowing epoxidation effluent. A solution of epoxybutene in the absorbent is removed from the base of the absorption vessel and a vapor comprising butadiene, inert diluent, oxygen and carbon dioxide components of the epoxidation effluent is removed from the top of the vessel.

The absorbents useful in the operation of the process of the present invention have a boiling point at ambient pressure of at least 100° C., preferably from about 110 to 260° C. Among the desirable properties of the absorbents are: (1) high affinity and capacity for apoxybutene absorption; (2) low specific heat; (3) low of reactivity with epoxybutene and by-products; (4) oxidative stability under absorption and distillation conditions; (5) low vapor pressure at absorber conditions to reduce losses in absorber off-gas; (6) is a liquid at the normal operating conditions of a plant; (7) does not form an azeotrope with epoxybutene or is easily separable from epoxybutene; and (8) has limited miscibility with water. Although no chemical species possesses all of these desirable characteristics, after extensive testing of candidate absorption solvents, we have found that certain classes of compounds are exemplary solvents for the present invention.

As used herein, the terms "absorbent" and "solvent" are used interchangeably for describing a material or composition that preferentially absorbs epoxybutene from a stream composed of the epoxybutene and other constituents. As used herein, "absorbent zone" and "absorber" are used interchangeably as one skilled in the art will recognize that each performs a substantially similar function and accordingly, will be referred to herein as "absorber".

Examples of absorption solvents within the scope of this invention include but are not limited to aliphatic and cyclic alcohols containing 4 to 25 carbon atoms; aliphatic and cyclic alkanes and alkenes containing 8 to 25 carbon atoms; aromatic hydrocarbons containing 7 to 25 carbon atoms, chloro-, fluoro-, and chlorofluoro-hydrocarbons containing 8 to 25 carbon atoms having boiling points greater than about 120° C.; aliphatic ethers containing 8 to 25 carbon atoms; cyclic ethers containing 10 to 25 carbon atoms; aliphatic ketones containing 6 to 25 carbon atoms; cyclic ketones containing 6 to 25 carbon atoms; aliphatic esters of alkanoic and aromatic carboxylic acids containing a total of 6 to 25 carbon atoms; glycol ether esters of alkanoic acids containing a total of 6 to 25 carbon atoms; alkyl and aryl carbonates containing 5 to 25 carbon atoms; and cyclic carbonates containing 2 to 25 carbon atoms; or mixtures of any two or more thereof.

Specific examples of useful absorbents include isooctane, n-octane, nonane, decane, undecane, dodecane, Stoddard solvent, VMP Naphtha, mixed aliphatic hydrocarbons exemplified by ExxonMobil solvents Isopar G, H, L, M, and Ashland Solvent 140, vinylcyclohexene, octenes, nonenes and decenes, limonene, toluene, p-xylene, m-xylene, o-xylene, mesitylene, 1,3-diisopropylbenzene, 1,2-diisopropybenzene, 1,4-diisopropylbenzene, 1-methyinaphthalene, 1,2,3,4-tetrahydronaphthalene, 1,2-dichlorobenzene, 1,3-dichlorobenzene, 1,4-dichlorobenzene, isobutylisobutyrate, 2,2,4-trimethyl-1,3-pentandiol diisobutyrate, isobutyl acetate, n-butyl acetate, n-butyl propionate, isobutyl propionate, n-propyl butyrate, isopropyl butyrate, isopropyl isobutyrate, n-butyl butyrate, 2-ethylhexyl acetate, methyl benzoate, isopentyl acetate, pentyl acetate, diisobutyl ketone, methyl amyl ketone, methyl isobutyl ketone, cyclohexanone, 2-methoxy-1-methylethyl acetate (propylene glycol monomethyl ether acetate), 2-methoxy-1-methylethyl propionate (propylene glycol monomethyl ether propionate), 2-methoxy-1-methylethyl butyrate (propylene glycol monomethyl ether butyrate), ethylene carbonate, propylene carbonate, butylene carbonate, vinylethylene carbonate, diethylcarbonate, dipropyl carbonate, dibutyl carbonate, diisobuytl carbonate, dibutyl ether, diisobutylether, and mixtures thereof. The preferred solvents have a boiling point of about 100 to 260° C. and low water solubility/miscibility, e.g., water solubility of less than about 10 weight percent, preferably less than about 5 weight percent, at ambient temperature. The most preferred high-boiling solvents comprise p-xylene, m-xylene, o-xylene, isobutyl acetate, n-butyl acetate, n-butyl propionate, isobutyl propionate, n-propyl butyrate, isopropyl butyrate, isopropyl isobutyrate, isopentyl acetate, pentyl acetate, methyl amyl ketone, methyl isobutyl ketone, propylene carbonate, butylene carbonate, vinylethylene carbonate, or a mixture of any 2 or more.

The amount of liquid absorbent fed to the absorber can vary substantially depending on, for example, the particular vessel configuration, the use of packing material and its type, and the feed rate and composition of the epoxidation effluent. Generally, the molar ratio of the absorbent feed to epoxidation effluent feed is in the range of about 15:1 to about 1:20, more typically about 3:1 to 1:5. The absorber and its contents typically are operated at a temperature between about 0 and 100° C. and at a pressure of about 1 to 17 bara, preferably at a temperature from about 20 to 70° C. and pressure of about 2.5 to 7.5 bara.

The effluents from the absorption zone comprise (1) a gaseous effluent comprising butadiene, oxygen and an inert diluent which exits the upper section or top of the absorption vessel and (2) a liquid effluent comprising epoxybutene, the absorbent, butadiene and water which exits the lower section or bottom of the absorption vessel. The amount of epoxybutene present in the gaseous effluent depends on the absorbent flow rate and the number of stages in the absorber but typically is less than 0.1 weight percent, preferably less than about 0.05 weight percent, and more preferably less than about 250 ppm. The gaseous effluent stream may be recycled to the epoxidation zone. When a significant amount of the butadiene present in the absorber feed gas is absorbed by the absorbent employed, additional butadiene may be fed to the absorber so that the butadiene concentration in the gaseous effluent is suitable for recycling to the epoxidation zone. Alternatively, any makeup butadiene required may be fed to the recycle stream at a point downstream from the absorber.

We have found that low levels, e.g., less than 500 ppmv, of substantially all oxygen- and/or nitrogen-containing, or aromatic species useful as epoxybutene absorbents in the process of the present invention can cause a reversible decrease in the activity of the silver epoxidation catalyst when present in the recycle gas to the epoxidation zone. The detrimental effect is generally proportional to the level of the solvent contained in the recycle gas. Thus, it is beneficial to keep the level of the solvent in the recycle gas to as low a level as practical and economical. Alkane type solvents do not adversely affect reactor performance. One method of minimizing the solvent level in the recycle gas is to use a solvent that is substantially non-volatile, i.e., has a partial pressure of less than about 0.009 bar at the temperature and pressure conditions at the top of the absorber.

A second method of minimizing the solvent level in the recycle gas, which may be employed separately or in conjunction with the choice of a very high-boiling solvent, is to cool absorber effluent gas stream in a partial condenser by indirect contact with a suitable cooling media such as water, glycol, or chilled brine. The preferred temperature for operation of the partial condenser is such that the vapor pressure of the solvent is less than about 0.033 bar at the temperature and pressure conditions at the exit of the partial condenser. Typically, the partial condenser operates at −25 to 45° C., more typically −10 to 30° C.

The liquid effluent comprising epoxybutene, the absorbent, butadiene and water which exits the lower section or bottom of the absorption vessel normally contains about 1 to 30 weight percent epoxybutene, about 0.1 to 30 weight percent water, 0.25 to 40 weight percent butadiene, about 30 to 98 weight percent high-boiling absorbent, and minor amounts of dissolved gases. The composition of the liquid effluent preferably comprises about 5 to 20 weight percent epoxybutene, about 0.5 to 10 weight percent water, and about 30 to 90 weight percent high-boiling absorbent. This liquid effluent is conveyed to a first distillation column (absorbent recovery column) wherein epoxybutene, water, and minor amounts of other materials such as butadiene, dissolved oxygen, nitrogen, carbon dioxide, methane or other inert reaction diluent, are stripped from the water-miscible solvent. The liquid effluent from the absorber is fed to the mid-section, preferably at least 2 theoretical equilibrium stages from the top, of the first distillation column. The section above the feed tray serves as a rectifying section to keep the absorbent out of the distillate. The preferred number of theoretical equilibrium stages in the first distillation column is 4 to 18 stages, preferably 6 to 12 stages. The temperature at the top stage of the first distillation column normally is from about 60 to 105° C., depending the water content of the overhead vapor distillate. The temperature at the base of the first distillation column normally is from about 100 to 270° C., preferably from about 100 to 200° C. The operating pressure of the first distillation column normally is within the range of about 1 to 4 bara, and preferably from about 1 to 2.3 bara.

A vaporous distillate product is removed from the upper section or top of the first distillation column and cooled to condense and separate a liquid product comprising epoxybutene and water from an uncondensed vapor comprising normally gaseous and low boiling components such as oxygen, nitrogen, carbon dioxide, methane or other inert reaction diluent saturated with epoxybutene, butadiene and water. The liquid product, which typically comprises about 9 to 70 weight percent water and 30 to 91 weight percent epoxybutene, is fed to a decanter wherein the liquid is allowed to settle and separate into two phases. The upper organic phase typically comprises about 90 to 98 weight percent epoxybutene, about 2 to 10 weight percent water, and a trace amount of butadiene. The lower aqueous phase typically comprises about 95 to 97 weight percent water and about 3 to 5 weight percent epoxybutene.

The butadiene and epoxybutene present in the uncondensed vapor from the first distillation column may be recovered by contacting the uncondensed vapor with cooling media at temperatures less than about −10° C. in a heat exchanger. Another method is by vapor recompression followed by heat exchange with a typical cooling media such as cooling water, chilled brine, or glycol. A third and preferred method is absorption in a counter-current absorption tower (butadiene recovery zone) using the same high-boiling, liquid absorbent as is used in the absorption zone. The absorbent-containing, recovered butadiene and epoxybutene may be conveyed to the absorption zone for further processing while the gases not dissolved by the absorbent may be vented. This method is preferred when a solvent with high affinity for butadiene is used as the absorbent in the absorption zone. Examples of useful solvents for butadiene recovery in the butadiene recovery zone are isooctane, n-octane, nonane, decane, undecane, dodecane, Stoddard solvent, VMP Naphtha, mixed aliphatic hydrocarbons exemplified by ExxonMobil solvents Isopar G, H, L, M, and Ashland Solvent 140, vinylcyclohexene, octenes, nonenes and decenes, limonene, toluene, p-xylene, m-xylene, o-xylene, mesitylene, 1,3-diisopropylbenzene, 1,2-diisopropybenzene, 1,4-diisopropylbenzene, 1-methylnaphthalene, 1,2,3,4-tetrahydronaphthalene, ethylene carbonate, propylene carbonate, butylene carbonate, vinylethylene carbonate, diethyl carbonate, dipropyl carbonate, dibutyl carbonate, diisobuytl carbonate, and mixtures of any two or more thereof. Optionally, the solvent used for butadiene recovery may be different than the solvent used for epoxybutene absorption. Examples of such optional solvents for butadiene recovery include acetonitrile, 1-methyl-2-pyrrolidinone (NMP), morpholine, dimethylformamide, dimethylacetamide, and other water-miscible polar aprotic solvents.

A liquid product comprising high-boiling absorbent, water, and epoxybutene-water reaction products, e.g., 1-butene-3,4-diol, 2 butene-1,4-diol, and higher epoxybutene-derived ether alcohols is removed from the lower section or base of the first distillation column and recycled to the absorption vessel. A portion of the underflow from the first distillation column may be passed through a heat exchanger and returned to the bottom section of the column to provide the heat to operate the first distillation column.

The water-rich lower liquid phase from the above-mentioned decanter is fed to the upper section near the top, e.g., within about three theoretical equilibrium stages from the top, of a second distillation column (water column) wherein epoxybutene is stripped from water. The second distillation column preferably contains 3 to 12 theoretical equilibrium stages, preferably 6 to 10 stages. The temperature at the top stage of the column is normally from about 60 to 105° C., depending upon the water content of the overhead vapor. A vaporous distillate product is removed from the top of the second distillation column and is cooled in a condenser by indirect contact with any typical cooling media such as cooling water, chilled brine, or glycol. The condensed overhead vapors comprising epoxybutene and water are conveyed to the above-mentioned decanter wherein the condensed liquid is allowed to settle and separate into two phases. The composition of the condensed liquid typically is on the water-rich side of the epoxybutene-water minimum-boiling azeotrope, and typically comprises about 10 to 99 weight percent water and 1 to 90 weight percent epoxybutene, more typically about 15 to 50 weight percent water and 50 to 85 weight percent epoxybutene.

A liquid product stream consisting essentially of water and trace amounts of epoxybutene and epoxybutene-waer reaction products, e.g. 3-butene-1,2-diol is removed from the base of the second distillation column and discarded from the recovery system. A portion of the underflow from the second distillation column may be passed through a heat exchanger (reboiler) and returned to the bottom section of the column to provide the heat to operate the second distillation column. The conditions employed within the water column can vary depending on the particular apparatus employed. The operating temperature of at the base of the water column normally is within the range of about 100 to 150° C., preferably from about 100 to 120° C. The operating pressure of the second distillation column normally is within the range of about 1 to about 4 bara, and preferably from about 1 to about 2.3 bara. Temperatures, pressures, and boilup rate are adjusted such that the lean water stream removed from the bottom of the water column comprises less than 0.1 weight percent, preferably less than 500 ppm by mass, more preferably less than 100 ppm by mass of epoxybutene.

The epoxybutene-rich, upper, liquid phase from the above-mentioned decanter is fed to a third distillation column (epoxybutene purification column) wherein water and any remaining butadiene is distilled (stripped) fîrom the epoxybutene. The epoxybutene-rich, aqueous layer is fed near the top, e.g., within about three theoretical equilibrium stages from the top, of the third distillation column. The preferred number of theoretical equilibrium stages in the epoxybutene purification column is 4 to 20 stages, preferably 6 to 15 stages. The temperature at the top stage of the epoxybutene purification column normally is from about 60 to 75° C., depending upon the water content of the overhead vapor. A vaporous distillate product is removed from the top of epoxybutene purification column and is cooled in a partial condenser by indirect contact with any typical cooling media such as cooling water, chilled brine, or glycol. A vapor consisting of low boiling components (light ends) comprising oxygen, nitrogen, carbon dioxide, methane or other reaction diluent, saturated with butadiene, epoxybutene, and water, are removed from the partial condenser. Butadiene and epoxybutene may be recovered from the low boiler stream by the same means described above for the vapor effluent from the first distillation column. The condensed vapor removed from the top of epoxybutene purification column comprising epoxybutene and water are returned to the decanter where the condensed liquids are allowed to settle and separate into two phases. The composition of the vapor from the top of epoxybutene purification column typically is on the epoxybutene-rich side of the epoxybutene-water minimum-boiling azeotrope, and typically comprises about 1 to 8 weight percent water and greater than about 90 weight percent epoxybutene.

A dehydrated epoxybutene product is removed from the base of the epoxybutene purification column. A portion of the underflow from the third distillation column typically is passed through a heat exchanger (reboiler) and returned to the bottom section of the column to provide the heat to operate the third distillation column. The conditions employed within the epoxybutene purification column can vary depending on the particular apparatus employed. The operating temperature at the base of the column normally is within the range of about 67 to 120° C., preferably from about 67 to 100° C. The operating pressure of the epoxybutene purification distillation column normally is within the range of about 1 to about 4 bara, and preferably from about 1 to about 2.3 bara. Temperatures, pressures, and boilup rate are adjusted such that the dehydrated epoxybutene product stream removed from the bottom of the epoxybutene purification column comprises less than 0.1 weight percent, preferably less than 500 ppm by mass, more preferably less than 150 ppm by mass, water.

Optionally, product epoxybutene may be withdrawn as a vapor or liquid side draw stream from the epoxybutene purification column, e.g., at least 1 theoretical stage above the reboiler. When epoxybutene product is withdrawn via a sidedraw stream from the epoxybutene purification column, a liquid removed from the base of the column comprises epoxybutene, higher boiling epoxybutene oligomers, extraction solvent, and 3-butene-1,2-diol by-products. Epoxybutene having a purity of greater than 99 weight percent, more preferably greater than 99.5 weight percent, may be obtained either from the base, or as a side draw from, the epoxybutene purification column.

The absorber and distillation columns which may be utilized in the operation of the process of the present invention typically comprise columnar, pressure vessels containing trays or a packing material that facilitates intimate gas/liquid contact. The gas/liquid contacting equipment in the columns may include, but is not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings™. These and other types of suitable gas/liquid contacting equipment are described in detail in Kister, H. Z. Distillation Design, McGraw-Hill, N.Y. (1992), Chapters 6 and 8 the disclosures of which are incorporated herein by reference.

To prevent the formation of butadiene polymerization products, absorption of epoxybutene in the absorber and the operation of the solvent recovery column and epoxybutene purification column may be carried out in the presence of a polymerization inhibitor known to those skilled in the art. For example, suitable polymerization inhibitors include tertiary butyl catechol or amine oxide compounds. The polymerization inhibitor may be added to the upper section of the absorber, the solvent recovery column, and the epoxybutene purification column. The formation of low molecular weight, butadiene polymerization products are substantially suppressed by the addition of about 300 to 400 ppm inhibitor, based on the amount of vapor removed from the column. The inhibitor addition point can be any place that is convenient for the operation of the columns by means of a low-flow addition device such as a syringe pump.

Epoxybutene reacts readily with nucleophiles such as water and alcohols to form 3-butene-1,2-diol and glycol ethers, respectively. However, the relative rate of epoxybutene reaction with nucleophiles is a function of pH. Epoxybutene, like other epoxides, undergoes both acid and base catalysis. Acid catalysis has the larger influence on the rate of reaction. For example, the rate of epoxybutene hydrolysis is over 500 times greater at pH 3 than at pH 7. At pH 11, the rate is over 17 times greater than at pH 7. Since it is desirable to minimize epoxybutene losses due to reaction with nucleophiles, epoxybutene reactivity can be reduced by maintaining the epoxybutene-laden solution at or near a pH of about 7 to 8. This can be done by adding a basic compound to the recovery system. Generally the process gas from the epoxidation reactor contains ppm levels of formic acid and other organic acids. Thus, any basic material which is capable of neutralizing organic acids may be used in the present process. Examples include Group Ia (alkali) metal hydroxides, bicarbonates, carbonates, and phosphates; Group IIa (alkali earth) metal hydroxides and carbonates; ammonia; ammonium hydroxide, bicarbonate, carbonate, and phosphate; amines such as tertiary amines, e.g., trialkyl amines containing up to about 18 carbon atoms; amino alcohols, such as tertiary aminoalkanols, e.g., N,N-dialkylaminoalkanols containing up to about 20 carbon atoms; basic ion-exchange resins, and similar materials. The use of phosphate buffers, ammonia, ammonium buffers, and/or alkyl amines are the preferred methods.

The buffer component or components are generally added to the absorption/distillation system as an aqueous mixture on an as needed basis to maintain the pH within the proper range. The buffer solution may be added to any or all of the absorber, decanter or second distillation (water) column.

Referring to the accompanying FIGURE, cooled reaction effluent from a butadiene epoxidation zone is fed via line 1 to the lower section of absorber 2 and high-boiling absorbent is fed via line 3 to the upper section of the absorber, preferably near the top. The absorbent flows downward countercurrent to the rising gaseous epoxidation effluent and absorbs epoxybutene from the gaseous effluent. A gaseous effluent comprising butadiene, oxygen, inert diluent and minor amounts of other compounds exits the upper section or top of the absorber 2 through line 5. The gaseous effluent of line 5 may be recycled to the butadiene epoxidation zone after some or all of the effluent has been treated, for example, in a carbon dioxide removal zone. To moderate the temperature within absorber 2, liquid may be removed via line 7, passed through heat exchanger 8 wherein the temperature of the liquid is lowered, and returned to the absorber through line 9.

Epoxybutene-rich absorbent is removed from the lower section or bottom of absorber 2 and conveyed via lines 6 and 10 to the mid-section of first distillation column 20 wherein epoxybutene, water, butadiene and other low boiling materials are separated from the water-miscible absorbent. The epoxybutene-rich absorbent is fed to the mid-section of column 20 and a vaporous product is removed from the column by line 21 and cooled in partial condenser 22. Non-condensed components comprising oxygen, nitrogen, carbon dioxide, methane and/or other process diluent and saturated with butadiene, epoxybutene and water are removed through line 23 and may be treated further as described above to recover the butadiene and epoxybutene components from the non-condensed stream.

Condensed liquids comprising epoxybutene and water are conveyed via conduit 24 to reflux decanter tank 40 wherein the condensed distillate, typically comprising about 9 to 70 weight percent water and 30 to 91 weight percent epoxybutene, is allowed to settle and separate into two phases. The upper, organic phase typically comprises 90 to 98 weight percent epoxybutene, about 2 to 3 weight percent water and butadiene. The lower, aqueous phase typically comprises about 95 to 97 weight percent water and 3 to 5 weight percent epoxybutene. Reflux is provided to column 20 by line 25. The reflux may be a fraction of the upper phase, a fraction of the lower phase or a mixed fraction of the upper and lower phases.

A liquid comprising high-boiling absorbent or solvent, water, and epoxybutene-water reaction products, i.e., 1-butene-3,4-diol, 2 butene-1,4-diol, and higher epoxybutene-derived ether alcohols is removed from the base of column 20 through line 26 and recycled to absorber 2 via line 27, heat exchanger 28, and line 3. Heat exchanger 28 may be utilized to adjust the temperature of the recycle liquid of line 27 to that desired for the absorbent fed to column 2, e.g., from about 0 to 100° C., preferably from about 20 to 70° C. Stream 10 may be heat-interchanged with stream 27 to improve the energy efficiency of the process. Fresh, make-up absorbent may be added to the recovery system by means of line 29.

A portion of column underflow 26 may be diverted through line 30, heat exchanger 31, and line 32 to provide the heat (boilup) required for the operation of absorbent recovery column 20. Some or all of the required heat may be provided in the form of steam or hot water fed to the base of column 20 via conduit 33 to steam strip epoxybutene from the recyclable bottoms absorbent product removed through line 26.

The water-rich, lower phase contained in decanter 40 may be fed to the upper section, e.g., within about three theoretical equilibrium stages from the top, of third distillation column (water column) 50 via conduit 41 and 42. The purpose of water column 50 is to strip epoxybutene from the aqueous phase from the decanter. A vaporous distillate product is removed from the top of the water column through line 51, cooled in condenser 52 to condense the distillate vapor, and the resulting liquid is conveyed by means of line 53 to decanter 40 for separation into two phases. The composition of the condensed liquid typically is on the water-rich side of the epoxybutene-water minimum-boiling azeotrope, and typically comprises about 10 to 99 weight percent water and 1 to 90 weight percent epoxybutene, more typically about 15 to 50 weight percent water and 50 to 85 weight percent epoxybutene. A liquid product comprising primarily water is removed via line 54 from the bottom or base of water column 50 and discarded. Water column 50 is operated in a manner so that the liquid water stream removed via line 54 comprises less than 0.1 weight percent, preferably less than 500 ppm by weight, more preferably less than 100 ppm by weight, epoxybutene. A portion of underflow stream 54 is diverted by means of line 55, heated in heat exchanger 56 and fed via line 57 to the lower section near the bottom of column 50 to provide the heat required for the operation of the column. Optionally, live steam or liquid water may be introduced into the bottom of column 50 via conduit 58 to provide a means for steam stripping of epoxybutene from the water removed through line 54.

The epoxybutene-rich, upper, liquid phase contained in decanter 40 is conveyed via line 43 to a second distillation column (epoxybutene purification column) at a point near the top of column 60, e.g., within about three theoretical equilibrium stages from the top. A vaporous distillate product is removed from the top of column 60 through line 61 and fed to partial condenser 62 wherein a portion of the distillate is condensed. The condensed liquids comprising epoxybutene and water are conveyed from partial condenser 62 by line 64 to decanter 40. The uncondensed components, e.g., oxygen, nitrogen, carbon dioxide, methane and/or other process diluent, saturated with butadiene, epoxybutene and water are removed through line 63 and normally are treated to recover the butadiene and epoxybutene present therein. The uncondensed stream of line 63 may be treated with and in the same manner as uncondensed stream 23 is treated for recovery of butadiene and epoxybutene. Condenser 22 and condenser 63 serve essentially the same function and, to conserve capital expense, may be physically the same piece of equipment.

Liquid, dehydrated, epoxybutene product is removed from the lower section or base of column 60 through line 65 and normally constitutes the final, purified epoxybutene product of the epoxybutene recovery and purification process described herein. By proper control of temperatures, pressures and boilup rate within column 60, the epoxybutene underflow product contains less than 0.1 weight percent, preferably less than 500 parts per million by weight (ppmw), and most preferably less than 150 ppmw, water. A portion of underflow stream 65 is diverted by means of line 66, heated in heat exchanger 67 and fed via line 68 to the lower section near the bottom of column 60 to provide the heat required for the operation of the column. If the epoxybutene product stream is withdrawn from column 60 via line 65, then said product will contain in addition to epoxbutene, higher boiling components such as epoxybutene oligomers and 3-butene-1,2-diol by-products formed in column 60 or introduced into column 60 via feed line 43.

Alternatively and preferably, liquid, dehydrated, epoxybutene product may be withdrawn as a vapor or liquid via line 69 from the side of column 60 (column sidedraw), preferably at least one theoretical stage above the feed of reboiler feed line 68. If stream 69 is withdrawn as a vapor, the product is condensed in condenser 70 and recovered as a liquid through line 71. When stream 69 is withdrawn as a liquid, condenser 70 can be used to cool the product. Epoxybutene product is withdrawn as sidedraw steam 69, stream 65 removed from the base of column 60 comprises epoxybutene containing higher boiling components such as epoxybutene oligomers and 3-butene-1,2-diol by-products. In accordance with the process of the present invention, it is possible to obtain epoxybutene of greater than 99 weight percent purity, preferably greater than 99.5 weight percent purity, from either line 65 or 71.

When the high-boiling absorbent solvent and the co-absorbed water are sufficiently immiscible and the liquid absorber effluent stream form two liquid phases upon settling, the epoxybutene-rich absorbent removed from the lower section or bottom of absorber 2 liquid advantageous may be conveyed via conduits 6 and 11 to decanter 80 for removal of a fraction of the water contained therein by settling and phase separation. The water-rich, lower liquid phase from decanter 80, comprising soluble epoxybutene and high-boiling solvent may be discarded as waste or, preferably, conveyed via lines 82 and 42 to water column 50 for recovery of epoxybutene and solvent. The water-rich phase is fed near the top, e.g., within about three theoretical equilibrium stages from the top, of distillation column 50. The epoxybutene-rich absorbent phase is conveyed via lines 81 and 10 to the mid-section, preferably at least 2 theoretical equilibrium stages from the top, of solvent recovery column 20.

EXAMPLES

The recovery and purification process provided by the present invention is further illustrated by the following examples. The percentages specified in the examples are by weight unless otherwise specified.

Example 1

The absorption affinity and selectivity of various high-boiling solvents for epoxybutene, water, and butadiene were determined for each candidate absorbent solvent specified in Table 1. Absorption coefficients were calculated for epoxybutene, water, and butadiene from experimental and estimated vapor/liquid equilibrium (VLE) data at 4.5 bara 50° C. wherein Absorption Coefficient is:

$$\text{Absorbtion coefficient} = \frac{\text{Mole Fraction of Component } i \text{ in Vapor Phase}}{\text{Mole Fraction of Component } i \text{ in Liquid Phase}}$$

wherein component i is epoxybutene, butadiene, or water. The absorption coefficient is measure of the affinity of the high-boiling solvent for epoxybutene, water, and butadiene. A low number, e.g., less than about: 1.4, indicates high affinity for the given solute. The relative absorption affinity of a solvent is calculated as the ratio of the absorption coefficients of butadiene to epoxybutene and water to epoxybutene. A large number indicates a high selectivity for epoxybutene over either water or butadiene. We have found that the solvents with the highest selectivities for epoxybutene over water generally have poor selectivities for epoxybutene over butadiene. Absorption coefficients and relative selectivities for epoxybutene, water, and butadiene for high-boiling solvents evaluated are set forth in Table I. The best solvents are those with the highest selectivities for epoxybutene over both water and butadiene.

TABLE I

| | Absorption Coefficient | | | Selectivity | |
|---|---|---|---|---|---|
| Absorption Solvent | Epoxybutene | Water | Butadiene | Epoxybutene/ Water | Epoxybutene/ Butadiene |
| n-Nonane | 0.34 | 147.0 | 1.28 | 433.6 | 3.8 |
| n-Decane | 0.33 | 148.0 | 1.24 | 449.8 | 3.8 |
| n-Undecane | 0.32 | 147.5 | 1.20 | 460.9 | 3.8 |
| Vinylcyclohexane | 0.24 | 731.0 | 1.47 | 2995.9 | 6.0 |
| Toluene | 0.15 | 254.8 | 1.80 | 1654.5 | 11.7 |
| p-Xylene | 0.21 | 461.0 | 1.92 | 2174.5 | 9.1 |
| 1,3-Diisopropylbenzene | 0.19 | 198.0 | 1.29 | 1031.3 | 6.7 |
| 1-Methylnaphthalene | 0.14 | 92.5 | 1.30 | 670.3 | 9.4 |
| 1,2-Dichlorobenzene | 0.22 | 5.1 | 2.13 | 23.4 | 9.8 |
| Isobutyl Isobutyrate | 0.13 | 16.0 | 1.11 | 123.1 | 8.5 |
| Butyl Acetate | 0.13 | 8.0 | 1.25 | 62.0 | 9.7 |
| 2-Ethylhexyl Acetate | 0.14 | 19.2 | 1.01 | 138.1 | 7.3 |
| 2-Methoxy-1-Methylethyl Acetate | 0.15 | 0.2 | 1.26 | 1.4 | 8.2 |

TABLE I-continued

| | Absorption Coefficient | | | Selectivity | |
| --- | --- | --- | --- | --- | --- |
| Absorption Solvent | Epoxybutene | Water | Butadiene | Epoxybutene/Water | Epoxybutene/Butadiene |
| Butylene Carbonate | 0.17 | 21.9 | 2.25 | 129.6 | 13.3 |
| Propylene Carbonate | 0.20 | 17.1 | 2.75 | 85.5 | 13.8 |
| Vinyl Ethylene Carbonate | 0.11 | 30.0 | 2.99 | 272.7 | 27.2 |
| Diethyl Carbonate | 0.11 | 10.8 | 1.59 | 95.6 | 14.1 |
| Dibutyl Ether | 0.20 | 16.4 | 1.07 | 84.1 | 5.5 |
| n-Butanol | 0.20 | 0.7 | 3.36 | 3.4 | 16.8 |
| n-Octanol | 0.21 | 2.3 | 2.0 | 11.1 | 9.5 |
| Methyl Isobutyl Ketone | 0.13 | 3.2 | 1.42 | 24.2 | 10.9 |

Example 2

This example illustrates the distillative recovery of epoxybutene from absorbent solvent as described hereinabove. The epoxybutene-rich absorbent phase organic stream from decanter 80 (of the FIGURE) comprising 6.6% epoxybutene, >0.1% water, 0.3% 3-buten-1,2-diol, and 93.1% p-xylene was distilled continuously in a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. The bottoms product was cooled in a small water-chilled stainless steel heat exchanger placed in line on the suction side of the pump. The distillate product flowed by gravity to a jacketed cooled receiver, which also functioned as a phase decanter. Thermocouples were provided at the reboiler and distillation head. The continuous run was about 10 hours in duration with a total feed of about 3028 grams. A reflux ratio of 3:1 was employed. The column was operated at about 1 bara pressure. During steady state operation the average distillate composition comprised about 20.4% water, 79.4% epoxybutene, and less than 0.2% 3-buten-1,2-diol. The distillate formed two liquid phases upon settling. The average bottoms product comprised 600 ppm by mass water, less than 300 ppm by mass epoxybutene, 0.65% 3-buten-1,2-diol and other high boilers, and 99.2% p-xylene. Less than 0.5% of the epoxybutene present in the feed reacted to form 3-buten-1,2-diol and higher diol oligomers and 99.5% of the unreacted epoxybutene was recovered in the distillate.

Examples 3–5

Epoxybutene-rich distillate phases produced in the manner described in Example 2 were distilled to demonstrate epoxybutene recovery in a distillation system consisting of a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. Since the feed mixture comprised little water, the pH of the feed mixture was not measured, nor was any buffer solution added.

The bottoms product was cooled in a small water-chilled stainless steel heat exchanger placed in line on the suction side of the pump. The distillate product flowed by gravity to a jacketed cooled receiver, which also functioned as a phase decanter. For all examples a reflux ratio of 1:1 was employed. Thermocouples were provided at the reboiler, and distillation head. Each continuous run was from eight to 12 hours in duration. Feed compositions and conditions for each example are given in Table II. In all examples the distillate separated into two phases upon standing. This two-phase mixture was decanted and stored separately as water-rich and epoxybutene phases.

Distillate and bottoms (column base) temperatures, system pressure, and measured pH of the feed and bottoms products are given in Table III. All sampled were analyzed by gas chromatography using a thermal conductivity detector. Mass balances were performed to determine percent distillate, distillate and bottoms compositions, percent epoxybutene loss, the recovery of unreacted epoxybutene, and oligomer make-rate. Mass balance and temperature data are presented in Table III. The following terms used in Tables II and III are defined herein as follows: Percent Distillate is the total mass of distillate collected divided by the total mass of material fed to the column×100 and Percent Epoxybutene Loss is the sum of the mass of epoxybutene collected in the distillate and the mass of the epoxybutene collected in the liquid column base product divided by the total mass of epoxybutene fed to the column×100. In Table II, the feed temperature (Temp) is given in °C., the pressure (Press) within the column is given in bars absolute, the total material fed (Total Feed) is given in grams and the composition of the feed is given as a weight percentage. In Table III, the temperature at the head or top of the column (Head Temp) and at the column reboiler (Reboiler Temp) are given in °C., and the compositions of the distillate and bottoms liquid are given as weight percentages.

Example 6

A water-rich distillate layer produced in the manner described in Example 2 was distilled to demonstrate epoxybutene removal in a distillation system consisting of a silvered, vacuum-jacketed glass Oldershaw column, equipped with a liquid-dividing distillation head, feed tray, reflux magnet, reflux timer, cooling water condenser, jacketed reboiler, pressure cage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. The pH of the feed mixture was adjusted to a value of 8 by the addition of a $K_2CO_3$—$H_3PO_4$ buffer solution. A reflux ratio of 1:1 was employed for this example.

The bottoms product was cooled in a small water-chilled stainless steel heat exchanger placed in line on the suction side of the pump. The distillate product flowed by gravity to a jacketed cooled receiver, which also functioned as a phase decanter. Thermocouples were provided at the reboiler, and distillation head. The continuous run was of 12 hours duration. Feed compositions and conditions are given in Table II. The distillate separated into two phases upon standing. This two-phase mixture was decanted and stored separately as water-rich and epoxybutene-rich phases.

All samples were analyzed by gas chromatography using a thermal conductivity detector. A mass balance was done to determine percent distillate, distillate and bottoms compositions, and percent epoxybutene loss. Mass balance and temperature data are presented in Table III. Recovery of Unreacted Epoxybutene, the mass of epoxybutene collected in the distillate divided by the sum of the mass of epoxybutene collected in the distillate and the mass of the epoxybutene collected in the liquid column base product×100, for Example 6 was 100%.

TABLE II

| | | | Feed Composition, weight percent | | | |
|---|---|---|---|---|---|---|
| Example | Press (bara) | Total Feed (g) | Water | 1,2-Diol | Epoxy-Butene | Oligomer |
| 3 | 0.98 | 2600.4 | 2.1 | 0.0 | 97.9 | 0 |
| 4 | 0.98 | 2611.0 | 2.0 | 0.01 | 98.0 | 0 |
| 5 | 0.98 | 4759.3 | 2.1 | 0.08 | 97.8 | 0 |
| 6 | 0.98 | 2579.1 | 96.92 | 0.09 | 3.0 | 0 |

TABLE III

| | | | | Distillate Composition | | | Bottoms Composition | | | | Epoxy-Butene Loss |
|---|---|---|---|---|---|---|---|---|---|---|---|
| Example | Top Temp | Reboiler Temp | Percent Distillate | Water | 1,2-Diol | Epoxy-Butene | Water | 1,2-Diol | Epoxy-Butene | Oligomer | |
| 3 | 63.6 | 68.6 | 38.16 | 4.9 | — | 94.9 | 0.01 | 0.04 | 99.92 | — | 0.02 |
| 4 | 62.5 | 68.6 | 42.7 | 5.0 | — | 95.0 | 0.02 | 0.08 | 99.84 | — | 0.04 |
| 5 | 64.8 | 69.0 | 70.61 | 2.8 | <0.01 | 97 | 0.04 | 0.50 | 99.4 | <0.01 | 0.052 |
| 6 | 96.7 | 102.1 | 9.3 | 23.9 | 0.08 | 76.0 | 99.9 | 0.1 | N/D* | N/D* | 1.5 |

*N/D = None detected

The invention has been described in detail with particular refere nce to preferred embodiments thereof, but it will be understood that variations and modifications can be effected within the spirit and scope of the invention.

We claim:

1. Process for the recovery of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises feeding the effluent to an absorption vessel wherein the effluent is intimately contacted with a high-boiling, liquid absorbent to obtain:

(1) a gaseous effluent comprising butadiene, oxygen and an inert diluent from the upper section of the absorption vessel; and (2) a liquid effluent comprising epoxybutene, the absorbent and water from the lower section of the absorption vessel;

wherein the absorbent has a boiling point at ambient pressure of at least 100° C.; epoxybutene is 3,4-epoxy-1-butene; and butadiene is 1,3-butadiene.

2. Process according to claim 1 wherein the absorbent is selected from aliphatic and cyclic alcohols containing 4 to 25 carbon atoms; aliphatic and cyclic alkanes and alkenes containing 8 to 25 carbon atoms; aromatic hydrocarbons containing 7 to 25 carbon atoms, chloro-, fluoro-, and chlorofluoro-hydrocarbons containing 8 to 25 carbon atoms having boiling points greater than about 120° C.; aliphatic ethers containing 8 to 25 carbon atoms; cyclic ethers containing 10 to 25 carbon atoms; aliphatic ketones containing 6 to 25 carbon atoms; cyclic ketones containing 6 to 25 carbon atoms; aliphatic esters of alkanoic and aromatic carboxylic acids containing a total of 6 to 25 carbon atoms; glycol ether esters of alkanoic acids containing a total of 6 to 25 carbon atoms; alkyl and aryl carbonates containing 5 to 25 carbon atoms; and cyclic carbonates containing 2 to 25 carbon atoms; or mixtures of any two or more thereof.

3. Process according to claim 2 wherein the absorption vessel is operated at a temperature of about 20 to 70° C. and a pressure of about 2.5 to 7.5 bars absolute, the substantially-gaseous effluent is fed to the lower section of the absorption vessel, the absorbent is fed to the upper section of the absorption vessel, and liquid effluent (2) comprises about 5 to 20 weight percent epoxybutene.

4. Process according to claim 3 wherein the high-boiling, liquid absorbent has a boiling point of about 110 to 260° C. and a water solubility of less than about 10 weight percent water in the high-boiling solvent at a temperature of about 25° C.

5. Process according to claim 3 wherein the absorbent is isooctane, n-octane, nonane, decane, undecane, dodecane, Stoddard solvent, VMP Naphtha, mixed aliphatic hydrocarbons exemplified by ExxonMobil solvents Isopar G, H, L, M, and Ashland Solvent 140, vinylcyclohexene, octenes, nonenes and decenes, limonene, toluene, p-xylene, m-xylene, o-xylene, mesitylene, 1,3-diisopropylbenzene, 1,2-diisopropybenzene, 1,4-diisopropylbenzene, 1-methylnaphthalene, 1,2,3,4-tetrahydronaphthalene, 1,2-dichlorobenzene, 1,3-dichlorobenzene, 1,4-dichlorobenzene, isobutyl isobutyrate, 2,2,4-trimethyl-1,3-pentandiol diisobutyrate, isobutyl acetate, n-butyl acetate, n-butyl propionate, isobutyl propionate, n-propyl butyrate, isopropyl butyrate, isopropyl isobutyrate, n-butyl butyrate, 2-ethylhexyl acetate, methyl benzoate, isopentyl acetate, pentyl acetate, diisobutyl ketone, methyl amyl ketone, methyl isobutyl ketone, cyclohexanone, 2-methoxy-1-methylethyl acetate, 2-methoxy- 1-methylethyl propionate, 2-methoxy-1-methylethyl butyrate, ethylene carbonate, propylene carbonate, butylene carbonate, vinylethylene carbonate, diethylcarbonate, dipropyl carbonate, dibutyl carbonate, diisobuytl carbonate, dibutyl ether, diisobutylether, or a mixture of any 2 or more thereof.

6. Process according to claim 3 wherein the absorbent comprises p-xylene, m-xylene, o-xylene, isobutyl acetate, n-butyl acetate, n-butyl propionate, isobutyl propionate, n-propyl butyrate, isopropyl butyrate, isopropyl isobutyrate, isopentyl acetate, pentyl acetate, methyl amyl ketone, methyl isobutyl ketone, propylene carbonate, butylene carbonate, vinylethylene carbonate, or a mixture of any 2 or more thereof.

7. Process for the recovery and purification of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises the steps of:

I. feeding the effluent to an absorption vessel wherein the effluent is intimately contacted with a high-boiling, liquid absorbent to obtain (1) a gaseous effluent comprising butadiene, oxygen and an inert diluent from the upper section of the absorption vessel and (2) a liquid effluent comprising epoxybutene, the absorbent and water from the lower section of the absorption vessel;

II. feeding the liquid effluent (2) of step I, to the middle section of a first distillation column to obtain (1) a distillate effluent comprising epoxybutene and water from the upper section of the distillation vessel and (2) a liquid effluent comprising the absorbent from the lower section of the distillation vessel;

III. allowing distillate (1) from step II, to form two phases comprising an epoxybutene-rich phase and a water-rich phase; and IV. feeding the epoxybutene-rich phase from step III, to the upper section of an epoxybutene purification distillation column to obtain (1) a distillate effluent comprising epoxybutene and water from the upper section of the distillation vessel; and (2) an effluent comprising (a) liquid epoxybutene from the lower section of the distillation column or (b) liquid or gaseous epoxybutene from the side of the distillation column;

wherein the absorbent has a boiling point at ambient pressure of at least 100° C. epoxybutene is 3,4-epoxy-1-butene; and butadiene is 1,3-butadiene.

8. Process according to claim 7 wherein the absorbent is selected from aliphatic and cyclic alcohols containing 4 to 25 carbon atoms; aliphatic and cyclic alkanes and alkenes containing 8 to 25 carbon atoms; aromatic hydrocarbons containing 7 to 25 carbon atoms, chloro-, fluoro-, and chlorofluoro-hydrocarbons containing 8 to 25 carbon atoms having boiling points greater than about 120° C.; aliphatic ethers containing 8 to 25 carbon atoms; cyclic ethers containing 10 to 25 carbon atoms; aliphatic ketones containing 6 to 25 carbon atoms; cyclic ketones containing 6 to 25 carbon atoms; aliphatic esters of alkanoic and aromatic carboxylic acids containing a total of 6 to 25 carbon atoms; glycol ether esters of alkanoic acids containing a total of 6 to 25 carbon atoms; alkyl and aryl carbonates containing 5 to 25 carbon atoms; and cyclic carbonates containing 2 to 25 carbon atoms; or mixtures of any two or more thereof.

9. Process according to claim 8 wherein the absorption vessel is operated at a temperature of about 20 to 70° C. and a pressure of about 2.5 to 7.5 bars absolute, the substantially-gaseous effluent is fed to the lower section of the absorption vessel, the absorbent is fed to the upper section of the absorption vessel, the liquid effluent (2) of step I, comprises about 5 to 20 weight percent epoxybutene, the first distillation column is operated at a top temperature of about 60 to 105° C. and a base temperature of about 100 to 200° C. and a pressure of about 1 to 2.3 bars absolute and the epoxybutene purification distillation column is operated at a top temperature of about 60 to 75° C. and a base temperature of about 67 to 120° C. and a pressure of about 1 to 2.3 bars absolute.

10. Process according to claim 9 wherein the high-boiling, liquid absorbent has a boiling point of about 110 to 260° C. and a water solubility of less than about 10 weight percent water in the high-boiing solvent at a temperature of about 25° C.

11. Process according to claim 9 wherein the absorbent is isooctane, n-octane, nonane, decane, undecane, dodecane, Stoddard solvent, VMP Naphtha, mixed aliphatic hydrocarbons exemplified by ExxonMobil solvents Isopar G, H, L, M, and Ashland Solvent 140, vinylcyclohexene, octenes, nonenes and decenes, limonene, toluene, p-xylene, m-xylene, o-xylene, mesitylene, 1,3-diisopropylbenzene, 1,2-diisopropybenzene, 1,4-cliisopropylbenzene, 1-methylnaphthalene, 1,2,3,4-tetrahydronaphthalene, 1,2-dichlorobenzene, 1,3-dichlorobenzene, 1,4-dichlorobenzene, isobutyl isobutyrate, 2,2,4-trimethyl-1,3-pentandiol diisobutyrate, isobutyl acetate, n-butyl acetate, n-butyl propionate, isobutyl propionate, n-propyl butyrate, isopropyl butyrate, isopropyl isobutyrate, n-butyl butyrate, 2-ethylhexyl acetate, methyl benzoate, isopenlyl acetate, pentyl acetate, diisobutyl ketone, methyl amyl ketone, methyl isobutyl ketone, cyclohexanone, 2-methoxy-1-methylethyl acetate, 2-methoxy-1-methylethyl propionate, 2-methoxy-1-methylethyl butyrate, ethylene carbonate, propylene carbonate, butylene carbonate, vinylethylene carbonate, diethylcarbonate, dipropyl carbonate, dibutyl carbonate, diisobuytl carbonate, dibutyl ether, diisobutylether, or a mixture of any 2 or more thereof.

12. Process according to claim 7 wherein epoxybutene product (2) from step IV. has a purity of greater than 99.5 weight percent epoxybutene.

13. Process according to claim 9 wherein the absorbent comprises p-xylene, m-xylene, o-xylene, isobutyl acetate, n-butyl acetate, n-butyl propionate, isobutyl propionate, n-propyl butyrate, isopropyl butyrate, isopropyl isobutyrate, isopentyl acetate, pentyl acetate, methyl amyl ketone, methyl isobutyl ketone, propylene carbonate, butylene carbonate, vinylethylene carbonate, or a mixture of any 2 or more thereof.

14. Process according to claim 7 wherein a buffer component or components is added to the absorption vessel of step I, or the distillation vessel of step IV, in a quantity sufficient to maintain pH within the vessels at or near a pH of about 7 to 8.

15. Process according to claim 14 wherein a buffer component is selected from Group Ia (alkali) metal hydroxides, bicarbonates, carbonates, and phosphates; Group IIa (alkali earth) metal hydroxides and carbonates; ammonia; ammonium hydroxide, bicarbonate, carbonate, and phosphate; amines; amino alcohols; and basic ion-exchange resins.

16. Process according to claim 7 wherein the water-rich phase of step III, is fed to the upper section of a second distillation column (water column) to obtain a vaporous distillate product comprising epoxybutene and water from the top of the column and a liquid product comprising water from the base of the reactor.

17. Process according to claim 16 wherein vaporous distillate product comprises about 15 to 50 weight percent water and 50 to 85 weight percent epoxybutene and liquid product consists essentially of water and trace amounts of epoxybutene and epoxybutene-water reaction products.

18. Process according to claim 16 wherein a buffer component or components is added to the second distillation column in a quantity sufficient to maintain pH within the second distillation column at or near a pH of about 7 to 8.

* * * * *